United States Patent
Kilian et al.

[11] Patent Number: 6,159,484
[45] Date of Patent: Dec. 12, 2000

[54] COSMETIC PREPARATIONS

[75] Inventors: Henryka Kilian; Hanna Kaczmarska; Jadwiga Wiejacka; Halina Jarzebiak; Danuta Kwiecińska; Ewa Macierzyńska, all of Łódź; Grażyna Kaszczyk, Gałkówek Duży, all of Poland

[73] Assignee: Fabryka Kosmetykow Pollena-Ewa Spolka Akcyjna, Poland

[21] Appl. No.: 09/217,327

[22] Filed: Dec. 21, 1998

[30] Foreign Application Priority Data

Sep. 1, 1998 [PL] Poland ..................................... 328291

[51] Int. Cl.[7] ............................... A61K 6/00; A61K 7/00; A61K 7/04; A61K 7/06; A61K 31/74
[52] U.S. Cl. ............................ 424/401; 424/61; 424/70.1
[58] Field of Search .............................. 424/61, 70.1, 401

[56] References Cited

U.S. PATENT DOCUMENTS 5,814,078  9/1998  Zhou et al. ................................. 607/1

*Primary Examiner*—Thurman K. Page
*Assistant Examiner*—S. Howard
*Attorney, Agent, or Firm*—Bauer & Schaffer, LLP

[57] ABSTRACT

The preparation consists of 0.05–5% by weight of nutritive substances, 0–20% by weight of fatty substances, 0.5–15% by weight of alcohol, 0–1.5% by weight of fragrance compound, 0.5–5% by weight of moisturizing substance, 0–20% by weight of emolient, 0.1–20% by weight of surface-active substances, 0.02–1.0% by weight of preserving agent, 0–5% by weight of conditioning agent, 0.1–25% by weight of flax glycerol-glycol-water biocomplex, 0–2.5% by weight of viscosity regulator and pH regulator depending upon the need.

4 Claims, No Drawings

COSMETIC PREPARATIONS

The subject of the invention are cosmetic preparations for skin, hair and nails care and beautifying.

There are known cosmetic preparations of the Polish patent No. P-316744 where there has been applied flax biocomplex being a mixture of multiple glycol-water extract of flax seed and modified flax seed oil obtained by cold extraction. This biocomplex is hereinafter called flax glycol-water biocomplex.

The process for obtaining cosmetic preparations with flax glycol-water biocomplex according to the patent P-316744 makes some problems particularly with production of the cosmetics which contain considerable quantity of water, especially tonics and shampoos.

Specific composition of flax glycol-water biocomplex causes difficulties in achieving good clarity of shampoos and tonics and in keeping appropriate consistence of other cosmetics.

The above mentioned problems could be eliminated due to application of flax glycerol-glycol-water complex for cosmetics production.

The glycerol-glycol-water complex is a mixture of multiple glycol-water extract of flax seed and glycerol-glycol-water extract obtained from flax seed after short-time microwaves action.

Application (use) of microwaves in the extraction process allows to obtain a better degree of active substances extraction.

Due to application of the flax glycerol-glycol-water biocomplex it is possible to eliminate or reduce to minimum the use of flax oil which is inconvenient from the technological point of view. Since, the method for obtaining the flax glycerol-glycol-water biocomplex provides higher concentration of active substances.

Modified flax oil is added in larger quantity only to the products where it is justified for obtaining desirable effect of cosmetic action.

It has been found out that application of the flax glycerol-glycol-water biocomplex as a component of cosmetic preparations allowed to obtain durable clarity of tonics and shampoos as well as appropriate consistence of other cosmetics.

High effectiveness of influence of the flax glycerol-glycol-water biocomplex on skin, hair and nails is provided by active substances contained in it, such as glycerides of linolic acid, linolenic acid and oleic acid as well as saturated acids, particularly stearic acid and palmitic acid, phytosterols and vitamins A, E and F. In the flax glycerol-glycol-water biocomplex there are also polysaccharides, cyanogenic glycosides—linamarine and lothaustraline, organic acids and amino-acids as well as sitosterol, cholesterol and proteins.

The cosmetic preparations according to the invention contain 0.05–5.0% by weight of nutritive substances, 0–20% by weight of fatty substances, 0.05–80% of alcohols, 0–1.5% by weight of fragrance compounds, 0.5–5% by weight of moisturizing substances, 0–20% by weight of emollients, 0.1–20% by weight of surface-active substances, 0.02–1.0% by weight of preserving agents, 0–5% by weight of conditioning agents, 0–2.5% by weight of viscosity regulators, 0.1–25% by weight of the flax glycerol-glycol-water biocomplex and pH regulators depending upon the need. The composition of the flax glycerol-glycol-water biocomplex together with the traditional components of cosmetic preparations guarantees high effectiveness of these preparations.

Creams with the flax glycerol-glycol-water biocomplex have extremely favourable properties smoothing, firming and moisturizing epidermis. Besides they grease and nourish skin. They also protect skin from noxious environmental factors and in case of irritation, they soothe its reddening and allergic reactions.

Cosmetic preparations used for hair care improve its condition increasing its fluffiness and giving it attractive and durable gloss and they also make combing and styling easier reducing its tendency to electrization.

Cosmetic preparations for hands care soothe palms irritation and reddening and they make nails harder.

The clue of the invention is explained by the following examples:

EXAMPLE 1

Cosmetic Preparation in the Foam Form

The following components (parts by weight) were introduced into a mixer,
surface-active agent—0.5
conditioning agent—2.0
skin and hair moisturizing agent—0.5
fragrance compound—0.2
preserving agents—0.5
flax glycerol-glycol-water biocomplex—5.0
distilled water up to 100

The components are mixed for about 20 minutes up to obtaining a mixture of uniform consistence.

The obtained mixture is pored to spray containers and propane-butane is added.

EXAMPLE 2

Cream for Hands and Nails Care

The following components (parts by weight) were introduced into production apparatus provided with an agitator.
surface-active agent—3.0
alcohol—4.5
pH regulator—0.30
emolient—2.6
fatty substances—5.5
moisturizing substances—1.5
preserving agents—0.4
fragrance compound—0.25
flax glycerol-glycol-water biocomplex—8.0
water up to 100

After 10 minutes of mixing and homogenization, the product is passed to be put into containers.

EXAMPLE 3

Flax Vanishing Cream

The following components (parts by weight) are introduced Into a tank:
surface-active substance—5.0
alcohols—3.0
fatty substances—5.0
moisturizing substances—4.0
nutritive substances—2.0
emollients—2.0
flax glycerol-glycol-water biocomplex—10.0
viscosity regulators—2.5
fragrance compound—0.2
water up to 100.0

The oil and water phase is mixed and homogenized. After being cooled and analysed it is put into containers.

EXAMPLE 4

Cosmetic Preparation in the Form of Shampoo

The following components (parts by weight) were introduced Into a mixer provided with an agitator.

active-surface agents—17.0
skin and hair moisturizing agent—0.5
nutritive agent—1.0
fragrance compound—0.2
preserving agents—0.23
pH regulator—0.1
viscosity regulator—2.0
flax glycerol-glycol-water biocomplex—1.0
water up to 100

After all the components are dissolved completely (3 hours) and viscosity is stabilised (12 hours), the product is put into containers.

EXAMPLE 5
Hair Spray
conditioning agents—5
flax glycerol-glycol-water biocomplex—15
moisturizing agents—0.5
fragrance compound—0.2
alcohol up to 100

The product is poured into spray tins and propane-butane is added.

What is claimed is:

1. Cosmetic preparations comprising, 0.05–5.0% by weight of nutritive substances, 0.5–80% by weight of alcohols, 0–1.5% by weight of fragrance compounds, 0.5–5% by weight of moisturizing substances, 0–20% by weight of emollients, 0.1–20% by weight of surface-active substance, 0.02–1.0% by weight of preserving agents, 0–5% by weight of conditioning agents, 0–2.5% by weight of viscosity regulators, 0.1–25% by weight of flax glycerol-glycol-water biocomplex and pH regulators depending upon the need.

2. The cosmetic preparation according to claim 1 wherein the glycol-water complex is selected from the group consisting of a mixture of multiple glycol-water extract of flax seed and a glycerol-glycol-water extract of flax seed obtained under short-time microwave action.

3. The cosmetic preparation according to claim 1, wherein the surface active substances selectedd from the group consisting of linoleic acid, mixtures of linoleic acid, oleic acid stearic acid and palmitic acid, phytosterol and vitamins A, E and F, glycerol glycol water biocomplex polysaccharide cyanogenic glycosides organic acids and amino acids, sitosterol, cholesterol and proteins.

4. The cosmetic preparation according to claim 3, wherein the cyanogeic glycosides is selected from the group consisting of linamarine and lothaustraline.

* * * * *